United States Patent [19]

Somers et al.

[11] Patent Number: 5,428,001
[45] Date of Patent: Jun. 27, 1995

[54] METHOD FOR COMBATING WEEDS AMONG MAIZE PLANTS

[75] Inventors: David A. Somers, Roseville, Minn.; William B. Parker, Ballwin, Mo.; Donald L. Wyse, Wyoming, Minn.; John W. Gronwald, Shoreview, Minn.; Burle G. Gengenbach, St. Paul, Minn.

[73] Assignee: Regents Of The University of Minnesota, Minneapolis, Minn.

[21] Appl. No.: 179,946

[22] Filed: Jan. 11, 1994

Related U.S. Application Data

[60] Continuation of Ser. No. 917,462, Jul. 21, 1992, Pat. No. 5,290,696, which is a division of Ser. No. 538,674, Jun. 18, 1990, Pat. No. 5,162,602, which is a continuation of Ser. No. 269,584, Nov. 10, 1988, abandoned.

[51] Int. Cl.⁶ .............. A01N 43/40; A01H 4/00
[52] U.S. Cl. ................ 504/130; 800/235; 800/DIG. 56; 435/240.5
[58] Field of Search ........... 504/105, 130; 100/200, 100/205, 230, 235, 250, DIG. 52, DIG. 55, DIG. 56; 435/240.49, 240.5

[56] References Cited

U.S. PATENT DOCUMENTS

| | | | |
|---|---|---|---|
| 4,326,358 | 4/1982 | Lawrence, Jr. et al. | 47/58 |
| 4,731,499 | 3/1988 | Puskaric et al. | 47/58 |
| 4,818,277 | 4/1989 | George | 504/214 |
| 4,874,421 | 10/1989 | Kleschick et al. | 504/105 |

FOREIGN PATENT DOCUMENTS

| | | |
|---|---|---|
| 0270356 | 6/1988 | European Pat. Off. |
| WO92/16101 | 10/1992 | WIPO |

OTHER PUBLICATIONS

"Influence of Environment on Corn (Zea mays) Tolerance to Sethoxydim", Weed Science, 1987, vol. 35:568-575, James A. Fawcett, et al.

"Selection and Characterization of Corn Cell Line Tolerant to Sethoxydim", NCWCC Proceedings, vol.42, 1987, William B. Parker et al.

"Selection and Characterization of Corn Cell Lines Tolerant to Sethoxydim", (Abstract 180) Feb. 3, 1988), W. B. Parker et al.

"Selection and Characterization of Sethoxydim Tolerant Corn Cell Lines", Third U of M Poster Session: Basic and Applied Bio-Medical Research in Academia and Industry (Abstract 103) May 25, 1988), William B. Parker et al.

"Selection of an Imidazolinone Tolerant Mutant of Corn", Abst. 6 Int. Congress Plant Tissue Cell Culture, Minneapolis, Minn. 4-8 Aug. 1986 (University of Minnesota, Minneapolis) at p. 437, P. C. Anderson and M. Georgeson.

"Cell Culture Selection of Herbicide Tolerant Corn", Agromony Abstract, ASA, Madison, Wis. (1985) at p. 56, P. C. Anderson and K. A. Hibberd.

(List continued on next page.)

Primary Examiner—Che S. Chereskin
Attorney, Agent, or Firm—Burns, Doane, Swecker & Mathis

[57] ABSTRACT

Maize plants are grown in a planting area that are tolerant of inhibition by a cyclohexanedione herbicide, an aryloxyphenoxypropanoic acid herbicide, or mixtures thereof, at levels which normally inhibit growth and development, wherein said tolerance is conferred by an altered acetylcoenzyme A carboxylase (ACCase) tolerant of inhibition by the herbicide at levels which normally inhibit the activity of an unaltered ACCase. Additionally, an effective quantity of the named herbicide is applied so that the weeds (e.g., grass) are killed and the maize plants are uninjured. A representative cyclohexandione herbicide is sethoxydim and a representative aryloxyphenoxypropanoic acid herbicide is haloxyfop. Competition for the maize crop posed by weeds effectively is eliminated.

15 Claims, 4 Drawing Sheets

OTHER PUBLICATIONS

"Cell/Tissue Culture and In Vitro Manipulation", Corn & Corn Improvement, Third Edition, G. F. Sprague et al., eds., American Society of Agronomy et al., pubs., Madison, Wis. (1988) at Chapter 5, p. 345 to 387, R. L. Phillips et al.

"Selection for Resistance to Paraquat in Maize Embryogenic Cell Cultures", Abstracts, 6th Int. Congr. Plant Tissue Cell Cult. Minneapolis, Minn. (1986) at p. 73, T. R. Bowman and J. Duvick.

"Tissue Culture Studies on Cereals", Plant Cell, Tissue and Organ Culture, Springer-Verlag, Berlin, pub. 144–159 (1977). Y. Yamada.

"Plant Regeneration in Tissue Cultures of Maize", Maize for Biological Research, Plant Mole, Biol. Assn., Charlottesville, Va., pp. 367 to 371 (1982), C. E. Green and C. A. Rhodes.

"Linkage Map of *Escherichia Coli* K-12, Edition 7", Microbiological Reviews, vol. 47, No. 2, pp. 180–230, (Jun. 1983), Barbara J. Backmann.

"Yeast Mutants Defective in Acetyl-Coenzyme A Carboxylase and Biotin: Apocarboxylase Ligase", Eur. J. Biochem, 111. 79–87 (1980), Masayoshi Mishina et al.

"Genetically Transformed Maize Plants from Protoplasts", Science, vol. 240, p. 204 to 206, (1987), Carol A. Rhodes et al.

"High Velocity Microprojectiles for Delivering Nucleic Acids into Living Cells", Nature, vol. 327, pp. 70–73 (1987), T. M. Klein et al.

"Stable Transformation of Soybean (Glycine Max) by Particle Acceleration", Biotechnology, vol. 6, pp. 923–926. (Aug. 1988), Dennis E. McCabe et al.

"Inhibiton of Plant Acetyl-Coenzyme A Carboxylase by the Herbicides Sethoxydim and Haloxyfop", Biochemical and Biophysical Research Communications, vol. 148, No. 3, 1039–1044 (Nov. 13, 1987), J. D. Burton et al.

"Selection for Tolerance to Sethoxydim in Corn Tissue Culture", NCWCC Proceedings, vol. 41, 93 (abstract) (1986), William B. Parker et al.

Burton, et al. (Nov. 13, 1987) Biochem. Biophys. Res. Comm. 148 (3):1039–1044.

METHOD FOR COMBATING WEEDS AMONG MAIZE PLANTS

This application is a continuation of application Ser No. 07/917,462, filed July 21, 1992, now U.S. Pat. No. 5,290,696 which is a division of application Ser. No. 07/538,674, file Jun. 18, 1990 (now U.S. Pat. No. 5,126,602), which is a continuation of application Ser. No. 07/269,584, filed Nov. 10, 1988 (now abandoned).

FIELD OF THE INVENTION

This invention relates to genes and enzymes which confer tolerance of herbicides in plants, plant tissues and seeds. In particular, the invention involves maize plants which are tolerant of herbicides, and which genetically transmit this characteristic to their progeny.

BACKGROUND OF THE INVENTION

1. Weed Control

The use of selective herbicides for controlling specific weeds or plants in crops has become almost a universal practice. The market for these herbicides approaches a billion dollars annually. Even with this extensive use, weed control remains a significant and costly problem for the farmer.

Present day herbicides used singly or in so-called tank mixes require careful management to be effective. Time and method of application and stage of weed plant development are critical to getting good weed control with herbicides. Application of large amounts of preemergence herbicides can result in a commitment to grow the same crop in subsequent years because of chemical persistence in the soil which prevents rotation with a crop sensitive to that herbicide. Furthermore, some weed species are simply resistant to the available herbicides. Therefore, the development of effective herbicides increases in importance every year, especially as other weeds are controlled and thus reduce interplant competition.

Weed control in maize is currently accomplished by soil application of herbicides that are applied before the crop emerges and prior to the observation of a weed problem. The preemergence herbicides currently used adequately control most dicot and monocot (grass) weeds in maize. However, annual grass weeds such as wild proso millet and wooly cupgrass and perennial grass weeds commonly escape preemergence weed control. Preemergence herbicides require rainfall for activation, and under low rainfall conditions they fail to control grass weeds in corn. Furthermore, some preemergence herbicides persist in the soil and several have been detected as groundwater contaminants. The options for controlling these escape grass weeds are very limited. A postemergence herbicide for grass weed control in maize would be very beneficial. An attractive alternative to developing new herbicides to combat this weed control problem in maize and/or to decrease the amount of herbicide carryover and groundwater contamination in maize fields from the existing herbicides is to develop maize hybrids or varieties that are tolerant to other existing herbicides that normally kill all monocot (grass) species. The herbicide POAST TM (BASF Corp., Parsippany, N.J.) kills most grasses, and is applied at lower rates than many preemergence herbicides. POAST TM is nonpersistent in the environment and therefore does not represent a groundwater contamination threat. POAST TM-tolerant maize would provide the producer with increased weed management flexibility because POAST TM could be applied when a grass weed problem was detected without risk of damage to the crop and only to the areas with a weed problem. Therefore, postemergence control of local weed problems would further decrease the amount of herbicide applied compared to existing preemergence weed control strategies.

2. Tissue Culture of Maize

Irrespective of the plant species, there are a number of common features that apply to most tissue culture programs. The technique of cell and tissue culture has been widely developed, and much work has been done on growth, metabolism and differentiation of tissue culture of dicotyledons (Yamada, 1977, in *Plant Cell, Tissue and Organ Culture.*, eds. Reinert and Bajaj, pp. 144–159, Springer-Verlag, Berlin). However, successful tissue culture studies with monocotyledons (e.g., the cereal crops such as maize, rice, wheat, barley, sorghum, oats, rye and millet) leading to plant regeneration are not as widely documented as with dicotyledons. Success is frequently dependent on choosing donor tissues for culture initiation which come from plants of appropriate genotype as well as physiological and development states. Other features which are obviously important include the organic and inorganic composition of the growth medium and the physical environment in which the cultures are grown.

The development of maize tissue cultures capable of plant regeneration was accomplished after the identification of appropriate genotypes and donor tissues (Green and Rhodes, 1982, in *Maize for Biological Research*, ed. W. F. Sheridan, pp. 367–371, Plant Molecular Biology Association, Charlottesville, Va.). The first method developed which regenerated plants from tissue cultures of maize used immature embryos as donor tissues. Another donor tissue from which regenerable tissue cultures of maize have been initiated are immature tassels. This tissue is the male flower and as it matures, it is responsible for pollen production. Immature embryos, inflorescences, and the few other tissues in cereals from which regenerating cultures have been initiated all have the common characteristic of juvenility. With N6 or Murashige-Skoog (MS) growth media (defined below in Example 3) and a synthetic auxin, such as 2,4-dichlorophenoxyacetic acid (2,4-D), tissue cultures develop rapidly from the scutellum of the embryos. The resulting cultures are developmentally heterogeneous and contain a variety of tissue types. Removal of the 2,4-D from the growth medium permits these cultures to produce large numbers of regenerated plants. Cultures of this type have proved capable of regenerating plants for up to three years.

Regenerated plants obtained from tissue cultures are grown to maturity in a glasshouse, growth chamber, or field. The progeny seed produced from crosses with regenerated plants permits the evaluation of subsequent generations. The basic tissue culture methods developed for corn have been extended to many other cereal species.

An interesting development in recent years has been the occurrence of somatic embryogenesis in tissue cultures of maize. Somatic embryogenesis is the process where cells from callus, suspension, or protoplast cultures develop into complete embryos similar to zygotic embryos produced in seeds. It is now possible to reliably initiate cultures of corn which have two important characteristics. One is that the callus cultures are friable, meaning that they are soft and loose in texture. This property is important because cultures of this type exhibit rapid growth and are facilitated in the initiation of suspension cell cultures. The other valuable attribute of these friable cultures is their ability to form very large numbers of somatic embryos. Microscopic examination reveals the presence of many small, organized structures on the surface of the callus. These structures are young somatic embryos at various developmental stages. These friable cultures will retain their embryogenic potential for as long as two years, and have shown the capacity to produce extremely large numbers of somatic embryos.

The somatic embryos in these friable calli develop to maturity when the cultures are transferred to medium containing an increased concentration of sucrose (e.g., 5–6%) and no hormones. After approximately two weeks of growth on this medium, many embryos have become quite mature. They germinate rapidly and grow into plants when placed on MS or N6 medium containing 2% sucrose. The plants are then established in soil and are grown to maturity.

It is now well-documented that a high level of genetic variability can be recovered from plant tissue culture. It is well documented that spontaneous genetic variability in cultured plant cells may be the result of mutation (Meredith and Carlson, 1982, in *Herbicide Resistance in Plants*, eds. Lebaron and Gressel, pp. 275–291, John Wiley and Sons, N.Y.). The frequency of mutants can also be increased by the use of chemical or physical mutagens. Some of this variability is of agronomic importance. Mutants for disease resistance have been obtained in sugar cane for Fiji disease, early and late blight in potato, and southern corn leaf blight in maize. In rice, maize, and wheat, considerable variability for traits inherited as single genes of plant breeding interest has been recovered, including time of seed set and maturation, seed color and development, plant height, plant morphology, and fertility.

3. Mechanisms of Herbicide Tolerance

There are three general mechanisms by which plants may be resistant to, or tolerant of, herbicides. These mechanisms include insensitivity at the site of action of the herbicide (usually an enzyme), rapid metabolism (conjugation or degradation) of the herbicide, or poor uptake and translocation of the herbicide. Altering the herbicide site of action from a sensitive to an insensitive form is the preferred method of conferring tolerance on a sensitive plant species. This is because tolerance of this nature is likely to be a dominant trait encoded by a single gene, and is likely to encompass whole families of compounds that share a single site of action, not Just individual chemicals. Therefore, detailed information concerning the biochemical site and mechanism of herbicide action is of great importance and can be applied in two ways. First, the information can be used to develop cell selection strategies for the efficient identification and isolation of appropriate herbicide-tolerant variants Second, it can be used to characterize the variant cell lines and regenerated plants that result from the selections.

4. Herbicide Tolerance Selection

Tissue culture methods have been used to select for resistance (or tolerance) using a variety of herbicides and plant species (see review by Meredith and Carlson, 1982, in *Herbicide Resistance in Plants*, eds. Lebaron and Gressel, pp. 275–291, John Wiley and Sons, N.Y.). For example, P. C. Anderson et al. in U.S. Pat. No. 4,761,373, disclose the use of tissue culture methods to produce maize plants resistant to herbicidal imidazolinones and sulfonamides. The resistance is due to the presence of altered acetohydroxy acid synthase which is resistant to deactivation by these herbicides.

5 Herbicidal Cyclohexanediones

Certain 1,3-cyclohexanediones exhibit general and selective herbicidal activity against plants. One such cyclohexanedione is sethoxydim {2-[1-(ethoxyimino)-butyl]-5-[2-(ethylthio)propyl]-3-hydroxy-2-cyclohexen-1-one}. Sethoxydim is commercially available from BASF (Parsippany, N.J.) under the designation POAST ™.

Other herbicidal cyclohexanediones include clethodim, (E,E)-(±)-2-[1-[[(3-chloro-2-propenyl)oxy]imino]propyl]-5-[2-(ethylthio)propyl]-3-hydroxy-2-cyclohexen-1-one; available as SELECT ™ from Chevron Chemical (Valent) (Fresno, Calif.); cloproxydim, (E,E)-2-[1-[[(3-chloro-2-prophenyl)oxy]imino]-butyl]-5-[2-(ethylthio)propyl]-3-hydroxy-2-cyclohexen-1-one; available as SELECTONE ™ from Chevron Chemical (Valent) (Fresno, Calif.); and tralkoxydim, 2-[1-(ethoxyimino)propyl]-3-hydroxy-5-mesitylcyclohex-2-enone, available as GRASP ™ from Dow Chemical USA (Midland, Mich.)

For purposes of reference in the present specification, the herbicides described in the two preceding paragraphs and other structurally related herbicidal compounds, are collectively referred to as the cyclohexanedione family of herbicides.

6 Herbicidal Aryloxyphenoxyproanoic Acids

Certain aryloxyphenoxypropanoic acids exhibit general and selective herbicidal activity against plants. In these compounds, the aryloxy group may be phenoxy, pyridinyloxy or quinoxalinyl. One such herbicidal aryloxyphenoxypropanoic acid is haloxyfop, {2-[4-[[3-chloro-5-(trifluoromethyl)-2-pyridinyl]oxy]phenoxy]-propanoic acid}, which is available as VERDICT ™ Dow Chemical USA (Midland, Mich.) Another is diclofop, {(±)-2-[4-(2,4-dichlorophenoxy)-phenoxy]-propanoic acid}, available as HOELON ™ from Hoechst-Roussel Agri-Vet Company (Somerville, N.J.).

Other members of this family of herbicides include fenoxyaprop, (±)-2-[4-[(6-chloro-2-benzoxazolyl)oxy]-phenoxy]propanoic acid; available as WHIP ™ from Hoechst-Roussel Agri-Vet Company (Somerville, N.J.); fluazifop, (±)-2-[4-[[5-(trifluoromethyl)-2-pyridinyl]oxy]phenoxy]propanoic acid; available as FUSILADE ™ from ICI Americas (Wilmington,, Del.); fluazifop-P, (R)-2-[4-[[5-(trifluoromethyl)-2-pyridinyl]oxy]phenoxy]propanoic acid; available as FUSILADE 2000 ™ from ICI Americas (Wilmington, Del.); and quizalofop, (±)-2-[4[(6-chloro-2-quinoxalinyl)oxy]phenoxy]propanoic acid; avialable as AS-SURE ™ from E. I. DuPont de Nemours (Wilmington, Del.).

For purposes of reference in the present specification, the herbicides referred to in the two preceding paragraphs and other structurally related herbicidal compounds, are collectively referred to as herbicidal aryloxphenoxypropanoic acids.

SUMMARY OF THE INVENTION

This invention is directed to agronomically important plants, plant tissues and plant seeds which are tolerant of inhibition by a herbicide at concentrations which normally inhibit the growth and development of those plants, plant tissues and plant seeds. The present invention contemplates the introduction of herbicide tolerance into certain monocotyledons, preferably maize. Other monocotyledons into which herbicide tolerance may be introduced by the present invention include other cereal crops such as rice, wheat, barley, sorghum, oats, rye, millet, turf and forage grasses, and the like In particular, this invention is directed to processes for the production of plants, plant tissues and plant seeds which contain an enzyme that is tolerant of inhibition by a herbicide at a concentration which normally inhibits the activity of this enzyme before alteration. This enzyme, an altered acetyl-coenzyme A carboxylase (EC 6.4.1.2) (ACCase), confers tolerance of certain herbicides in plants, plant tissues and seeds, preferably to certain herbicides in maize plants, maize plant tissues, and maize seeds. The maize plants to which this invention is directed are tolerant of these herbicides at levels which inhibit the growth of the plants not comprising the altered ACCase This invention is also directed to processes and compositions for making and utilizing this altered enzyme, as well as the gene encoding the tolerant enzyme. One particular embodiment of the present invention is directed to the production of a herbicide-tolerant maize cell line possessing an alteration at the primary site of action of a herbicide. The present invention utilizes cell culture technology to isolate, characterize and develop herbicide-tolerant maize lines which genetically transmit this herbicide tolerance characteristic to their progeny. Other maize cell lines that are herbicide-tolerant exhibit elevated levels of the normal herbicide-sensitive maize ACCase.

The present invention also provides a method of generating plants, plant tissues and seeds, preferably maize plants, maize plant tissues, and maize seeds, from these tolerant cell lines which contain a gene coding for an altered ACCase which is tolerant of inhibition by a herbicide at a concentration which normally inhibits the activity of this enzyme before alteration.

In the examples presented herein, a novel enzyme, an altered ACCase which is tolerant of inhibition by members of the cyclohexanedione family of herbicides and members of the aryloxyphenoxypropanoic acid class of herbicides (at concentrations which normally inhibit the activity of the unaltered enzyme) is described. This enzyme confers tolerance of the herbicides in plants, plant tissues and seeds, preferably in maize plants, maize plant tissues and maize seeds. Maize genotypes expressing this altered ACCase are described. In the field, these maize genotypes may be used with these herbicides to effectively combat grass weed problems in maize production.

The present invention further contemplates that herbicide tolerance of the compounds described herein may be conferred by a variety of other mechanisms. For example, tolerance may be conferred by a gene coding for an enzyme which may be obtained from any source including, but not limited to, dicotylenous plants which possess herbicide tolerance due to altered ACCase, or the gene may be made in whole or part by chemical or enzymatic synthetic methods.

It is to be understood that the following detailed description presents a single embodiment of the invention. This embodiment relates to an alteration in a particular enzyme, ACCase, which renders certain maize plants, maize plant tissues, and maize seeds tolerant of certain cyclohexanediones, e.g., sethoxydim, as well as to certain aryloxyphenoxypropanoic acid herbicides, e.g., haloxyfop. Certain of these maize plants, maize plant tissues, and maize seeds were unexpectedly found to exhibit much higher levels of tolerance of sethoxydim than of haloxyfop. Also unexpectedly, certain other maizeplants, maize plant tissues, and maize seeds were found to be tolerant only of haloxyfop. Thus, the altered enzyme disclosed herein may confer tolerance of herbicides which inhibit ACCase as their primary site of action.

DETAILED DESCRIPTION OF THE INVENTION

Figure 1:
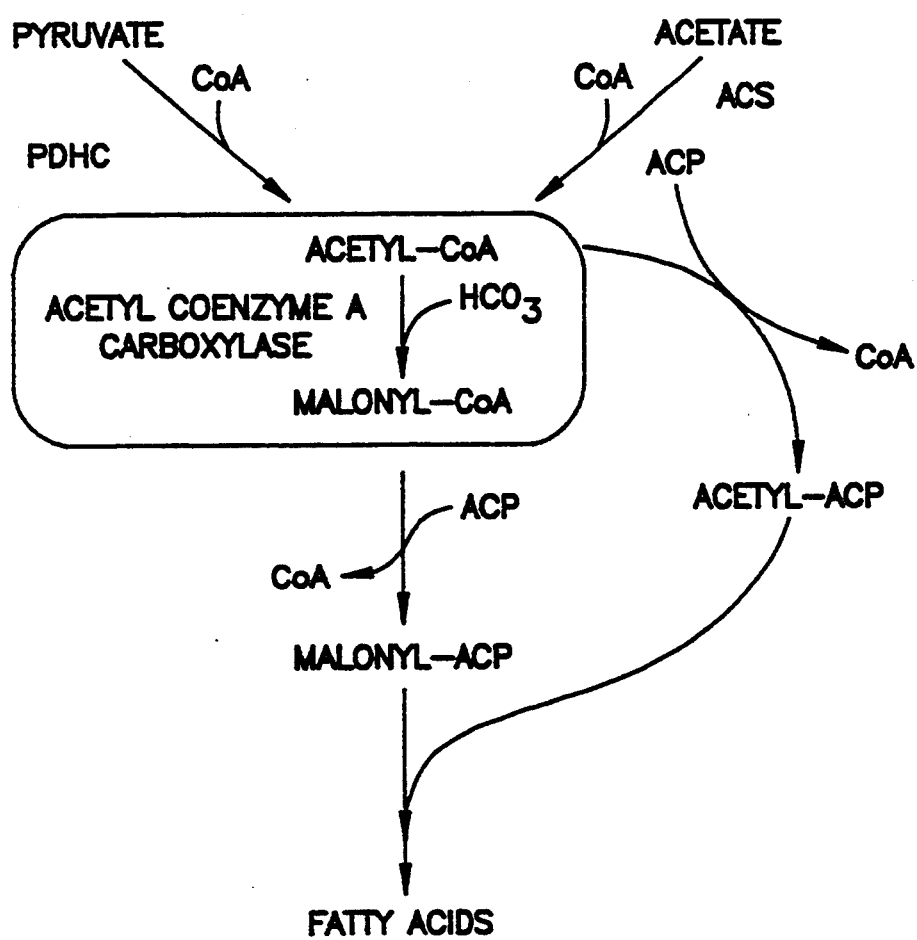
FIG. 1 is a schematic depiction of the fatty acid biosynthesis pathway in plants.

This embodiment of the invention relates to maize plants, maize plant tissues such as calli, and maize plant seeds which contain an enzyme which is tolerant of inhibition by cyclohexanedione and/or aryloxyphenoxy-propanoic acid herbicides The enzyme is an altered acetyl-coenzyme A carboxylase (ACCase) which confers tolerance of the above-mentioned herbicides in plants, plant tissues and seeds Methods and compositions are provided for producing maize plants, maize plant tissues and maize seeds containing a gene coding for an altered ACCase. Also described are cell culture selection techniques to select for novel maize genotypes tolerant of cyclohexanediones and/or aryloxyphenoxypropanoic acid herbicides. The production of these maize lines encompasses isolation, characterization, and development of these maize lines, as well as regeneration of maize plants from these cultures which are tolerant of the herbicides.

The description of the invention may be divided into the following areas: (1) determination of the primary site of action of the cyclohexanedione and/or aryloxyphenoxypropanoic acid families of herbicides; (2) characterization of the effects of these herbicides on maize cell cultures and the strategy for selection of herbicide-tolerant cell lines; (3) selection and characterization of herbicide-tolerant maize cell lines; (4) regeneration of herbicide-tolerant maize plants and production of maize seed; and (5) development of herbicide-tolerant commercial hybrid maize seed.

1. Determination of the Primary Site of Action of the Cyclohexanedione and/or Aryloxyphenoxypropanoic Acid Families of Herbicides The biochemical site of action of the herbicides, including but not limited to, sethoxydim and haloxyfop herbicides, in maize tissue is determined by first evaluating which general cell metabolic processes are affected by tissue exposure to the phytotoxic compounds. The specific site of action is then localized by in vitro evaluation of the individual reactions within the affected metabolic pathway or process.

The primary site of action may be determined by adding to tissue exposed to herbicide various labelled starting materials of the pathway(s) which is suspected to be affected by the herbicide. The failure of the pathway to utilize these starting materials in the presence of the herbicide indicates the pathway(s) affected by the herbicide.

2. Characterization of the Effects of the CyclohexaneDione and/or Aryloxyphenoxypropanoic Acid Families of Herbicides on Maize Plant Cell Cultures and Strategy for Selection of Herbicide-Tolerant Maize Cell Lines Efficient selection of a desired herbicide-tolerant mutant using tissue Culturetechniques requires careful determination of selection conditions. These conditions are optimized to allow growth and accumulation of rare herbicide-tolerant cells in the culture while inhibiting the growth of the bulk of the cell population. The situation is complicated by the fact that the viability of individual cells in a population is highly dependent on the viability of neighboring cells.

Conditions under which cell cultures are exposed to the herbicides of interest are determined by the characteristics of the interaction of the compounds with the tissue. Such factors as the accumulation of the compounds by cells in culture, and the persistance and stability of the compounds, both in the media and in the cells, need to be considered. Also important is whether the effects of the compounds can be readily reversed following their removal. Aside from factors associated with the chemistry of the herbicidal compounds, their effects on culture viability and morphology need to be carefully evaluated. It is especially important to choose herbicide exposure conditions which have no impact on plant regeneration capability of cultures. Choice of herbicide exposure conditions is also influenced by whether the herbicide kills cells or simply inhibits cell divisions.

The choice of a selection protocol is dependent upon the considerations described above. Either of the protocols briefly described below may be utilized in the selection procedure, although the present invention is not limited to these procedures. In the first protocol, finely divided cells in liquid suspension culture are exposed to high herbicide levels for brief periods of time. Surviving cells are then allowed to recover and accumulate, and are then reexposed for subsequently longer periods of time. Alternatively, organized, partially differentiated cell cultures are grown and subcultured with continuous exposure to initially low herbicide levels. Herbicide concentrations are then gradually increased over several subculture intervals.

3. Selection and Characterization of Tolerant Maize Cell Lines

Selections are carried out until maize cells or tissue are recovered which are observed to be growing well in the presence of normally toxic herbicide levels. These cell "lines" are then repeatedly subcultured in the presence of herbicide and characterized. The amount of tolerance which has been obtained is determined by comparing the growth of these cell lines with the growth of unselected cells or tissue in the presence of various herbicide concentrations. Stability of the herbicide tolerance trait of the cultured cells may be evaluated by simply growing the selected cell lines in the absence of herbicide for various periods of time and then analyzing growth after reexposing the tissue to herbicide.

In the present invention, maize cell lines which are tolerant by virtue of having an altered herbicide site of action are of primary interest. Maize cell lines may also be tested for tolerance of herbicides structurally related to the selection agent, such as the metabolites thereof.

The tolerant maize cell lines may also be evaluated using in vitro chemical studies to verify that the site of action of the herbicide is altered to a form which is less sensitive, or simply increased in expression.

4. Maize Plant Regeneration and Production of Maize Seed

Maize cell lines exhibiting satisfactory levels of tolerance by virtue of having an altered herbicide site of action are put through a plant regeneration protocol to obtain mature maize plants and seeds expressing the tolerance trait. The plant regeneration protocol allows the development of somatic embryos and the subsequent growth of roots and shoots. To determine that the herbicide-tolerance trait is expressed in differentiated organs of the plant and not ,solely in undifferentiated cell culture, regenerated plants are exposed to herbicide levels which will normally inhibit shoot and root formation and growth.

Mature maize plants are then obtained from maize cell lines that are known to express the trait. If possible, the regenerated plants are self-pollinated. Otherwise, pollen obtained from the regenerated plants is crossed to seed-grown plants of agronomically important inbred lines. Conversely, pollen from plants of these inbred lines is used to pollinate regenerated plants. The genetics of the trait are then characterized by evaluating the segregation of the trait in first and later generation progeny. The heritability and expression in maize plants of traits selected in tissue culture are of particular importance if the traits are going to be commercially useful.

5. Development of Herbicide-Tolerant Commercial Hybrid Maize Seed

Seed from maize plants regenerated from tissue culture is grown in the field and self-pollinated to generate true breeding plants. The progeny from these plants become true breeding lines which are evaluated for herbicide tolerance in the field under a range of environmental conditions. Herbicide tolerance must be sufficient to protect maize plants at the maximum labelled delivery rate under field conditions which cause the herbicides to be most active. Appropriate herbicide concentrations and methods of application are those which have been developed for the herbicides in question.

The commercial value of herbicide-tolerant maize is greatest if many different hybrid combinations with tolerance are available for sale. The farmer typically grows more than one kind of hybrid based on such differences as maturity, standability or other agronomic traits. Additionally, hybrids adapted to one part of a country are not adapted to another part because of differences in such traits as maturity, disease and insect tolerance. Because of this, it is necessary breed herbicide tolerance into a large number of parental lines so that many hybrid combinations can be produced Adding herbicide tolerance to agronomically elite lines is most efficiently accomplished when the genetic control of herbicide tolerance is understood. This requires crossing tolerant and sensitive plants and studying the pattern of inheritance in segregating generations to ascertain whether the trait is expressed as dominant or recessive, the number of genes involved, and any possible interaction between genes if more than one are required for expression. This genetic analysis can be part of the initial efforts to convert agronomically elite, yet sensitive, lines to tolerant lines.

A conversion process (backcrossing) is carried out by crossing the original tolerant line with a herbicide-sensitive elite line and crossing the progeny back to the sensitive parent. The progeny from this cross will segregate such that some plants carry the tolerance gene(s) whereas some do not. Plants carrying the tolerance gene(s) will be crossed again to the sensitive parent resulting in progeny which segregate for tolerance and sensitivity once more. This is repeated until the original sensitive parent has been converted to a tolerant line, yet possesses all of the other important attributes originally found in the sensitive parent. A separate backcrossing program is implemented for every sensitive elite line that is to be converted to a herbicide-tolerant line.

Subsequent to the backcrossing, the new tolerant lines and the appropriate combinations of lines which make good commercial hybrids are evaluated for herbicide tolerance, as well as for a battery of important agronomic traits. Tolerant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid seed corn production practices.

6. Alternative Methods of Obtaining Herbicide-Tolerant Mutants

Generally, any alteration or replacement of ACCase which leads to herbicide tolerance in tissue culture, seed and regenerated plants may be utilized in this embodiment of the present invention. ACCase may be altered or replaced in any plant species; of especially great importance are the agronomic and horticultural crops in which herbicides are utilized. Such plants include, for example, monocotyledenous plants, e.g., cereal crops such as maize, rice, wheat, barley, sorghum, oats, rye and the like. The alteration of ACCase may be accomplished by any of a variety of means, including but not limited to the following methods: (1) spontaneous variation and direct mutant selection tissue cultures; (2) direct or indirect mutagenesis procedures on tissue cultures of all types, seeds or plants; and (3) isolation of genes, manipulation, modification, or synthesis in whole or part of genes using molecular biology, chemical technologies, and state-of-the-art procedures and reintroduction of herbicide-tolerant genes into plants.

Additionally, any type of ACCase modification which leads to a change in tolerance of chemical compounds applied to plants may be utilized. These changes may include alterations in enzyme structure and changes in enzyme expression and/or function. Chemical compounds include not only those which may be synthesized by techniques of organic chemistry, but also naturally occurring compounds which may affect ACCase activity in the plant. Herbicide tolerance may also be accomplished by replacement or supplementation (i.e., gene therapy or the addition of extra genes), by any means, of an endogenous ACCase with any other ACCase from another source, including but not limited to prokaryotic or eukaryotic organisms or by a total or partial chemical synthesis of a gene that catalyzes the same reactions as ACCase.

Acetyl coenzyme A carboxylase (ACCase) catalyzes the carboxylation of acetyl coenzyme A to malonyl coenzyme A in the fatty acid biosynthesis pathway, as shown in FIG. 1 In most monocot plants ACCase is completely inhibited by both sethoxydim and haloxyfop. One known monocot exception is red fescue (*Festuca rubrum*), which is herbicide-tolerant due to the presence of a naturally herbicide-tolerant form of ACCase. It is believed that all dicot plants, yeast and other fungi and bacteria including *E. Coli* are tolerant of sethoxydim and haloxyfop due to the herbicide-tolerant ACCase. Therefore, herbicide-tolerant ACCase genes from herbicide-tolerant red fescue, from yeast and bacteria, and from dicot plants including but not limited to Arabidopsis, can provide a diverse source of genes which can be transferred into maize to confer herbicide tolerance.

Another source of herbicide-tolerant genes would be to use in vitro mutagenesis of wild type herbicide sensitive maize ACCase genes in bacteria or yeast, followed by reintroduction of the resulting herbicide-tolerant gene back into maize. This could be accomplished by complementing an auxotrophic mutant of ACCase in *E. coli* (fabE) (Bachman, *Microbiological Reviews*, 47, 180 (1983)), or yeast (accl), (Mishina et al., *Eur. J. Biochem.*, 111:79– 87 (1980)), with the wild type sensitive form of the maize gene. The maize ACCase gene would restore ACCase activity in the *E. coli* or yeast mutant strain that was previously missing the enzyme activity. Because the wild type maize gene would replace the *E. coli* or yeast gene's function, this would confer herbicide sensitivity to these organisms. Following ultraviolet light mutagenesis, herbicide-tolerant *E. coli* or yeast mutants would be selected on herbicide containing media. The maize gene (now herbicide-tolerant) would then be reisolated from the *E. coli* or yeast for reintroduction into sensitive maize plants.

Based on the elevated levels of ACCase activity in maize cell line 2167-9/2160-154 H-2, disclosed herein below, it is apparent that over-expression of the wild type ACCase gene confers herbicide tolerance. In this case, the wild type, herbicide sensitive maize ACCase gene would be placed under control of a gene transcription promoter which would ultimately increase the level of ACCase activity in the plant. For example, wild type maize ACCase would be placed under control of the 35S promoter of cauliflower mosaic virus. Modification of the promoter sequence can be used to manipulate the promoter strength so as to increase the expression of ACCase activity. This gene construct would be transferred back into maize.

Gene transfer into maize can be affected by either direct DNA uptake by maize protoplasts (Rhodes et al., *Science*, 240, 204 (1988)); microinjection into cells as described for oats (Bregitzer et al., *Agron Abstracts*, p. 166 (Nov. 27, 1988)), or by micro-projectile or particle acceleration (Klein et al., *Nature*, 327, 70 (1986); McCabe et al., *Biotechnology*, 6, 923 (1988); European Patent Application No 87310612.4). The DNA constructs will include either the wild type maize ACCase gene under control of strong promoters, or herbicide-tolerant maize ACCase genes, genes from red fescue, and other herbicide-tolerant genes derived from any dicot, fungi or bacteria. These genes may be under the control of the maize ACCase gene promoter or any other promoter that controls transcription in maize. Target tissues include protoplasts and cells from maize tissue cultures (callus and suspension), maize shoots and maize pollen. Transformed protoplasts, cells and/or plants and progeny will likely be selected directly for herbicide tolerance. In cases where heterologous gene transfer is effected and it is not known that the heterologous gene, e.g. from Arabidopsis, will function properly in maize, an additional selectable marker gene will be included with the ACCase DNA. This gene will likely encode tolerance of an antibiotic, e.g., kanamycin or methotrexate. Such a selectable marker gene is used to select transformed maize protoplasts, cells, tissue cultures or plants. Maize tissues selected for transformation by this second approach will be tested for herbicide tolerance.

The invention will be further described by reference to the following detailed examples.

EXAMPLE I

Identification of Herbicide Mechanism and Site of Action

The objective of this Example was to identify the mechanism whereby sethoxydim and/or haloxyfop inhibit fatty acid synthesis in maize. The results, reported in J. D. Burton et al., *Biochem. Biophys. Res. Comm.*, 148, 1039 (Nov. 13, 1987), show that both sethoxydim and haloxyfop inhibit acetyl-coenzyme A carboxylase (ACCase) (EC 6.4.1.2) in maize chloroplasts.

A. Chemicals.

Buffers and cofactors were purchased from Sigma Chemical Company (St. Louis, Mo.); [2-$^{14}$C]acetate was purchased from Research Products International; [2-$^{14}$C]pyruvate and [$^{14}$C]NaHC$_3$ were purchased from New England Nuclear; and [2-$^{14}$C]malonyl coenzyme A was purchased from Amersham. Sethoxydim was a gift from BASF (Parsippany, N.J.), and haloxyfop was provided by Dow Chemical USA (Midland, Mich.).

B. Plant Growth Conditions.

Corn (*Z. mays L.*,'B37×Oh43') seeds were germinated in darkness for 96 hr in vermiculite in an incubation chamber maintained at 30° C., 80% RH. Seedlings were then transferred to a growth chamber with a 16 hr light (25° C.) and an 8 hr dark (20° C.) cycle, 90% relative humidity (RH). After greening 48 hr, seedlings were returned to the dark incubation chamber for 12 hr to deplete chloroplast starch reserves. Seedlings were harvested 6 days after planting Pea (*P. sativum L.*, 'PI 9901-C') seedlings were grown in vermiculite in a growth chamber with a 16 hr light (21° C.) and 8 hr dark (16° C.) cycle, 80% RH. Peas were harvested 10 to 13 days after planting. Black Mexican Sweet (BMS) corn suspension cultures were maintained in a supplemented Murashige-Skoog (MS) medium (C. E. Green, *Hort Sci.*, 12, 7–10 (1977)), and subcultured weekly by 20-fold dilution of the suspension culture into fresh medium.

C. Chloroplast Isolation.

Chloroplasts from corn and pea seedlings were isolated at 4° C. (K. Cline et al., *J. Biol. Chem.*, 260, 3691–3696 (1985)). Seedlings (50 g of shoots) were homogenized in 200 ml buffer A (50 mM HEPES-NaOH pH 7.5, 330 mM sorbitol, 0.1% w/v BSA, 1 mM MgCl$_2$, 1 MnCl$_2$,2 mM EDTA, 5 mM isoascorbate, 1.3 mM glutathione) in an omnimixer (five, 3-sec bursts at full speed). The homogenate was filtered through six layers of cheesecloth and two layers of miracloth, and then centrifuged at 3000 g for 3 min with hand-braking The pellet was gently resuspended in buffer A and layered onto a preformed linear Percoll gradient: (50 mM HEPES-NaOH pH 7.5, 330 mM sorbitol, 1.9 mM isoascorbate, 1.08 mM glutathione, 0.1% w/v BSA, 50% Percoll) which was centrifuged at 3000 g for 20 min in a Sorvall HB-4 rotor. The lower band in the gradient, containing intact chloroplasts, was washed twice by gently resuspending it in 20 ml of buffer B (50 mM HEPES-NaOH, pH 7.5,and 330 mM sorbitol) followed by repelleting (3000 g, 5 min). The final pellet, consisting of intact chloroplasts, was resuspended in 2 to 3 ml of buffer B and stored on ice in the dark until use.

D. Fatty Acid Synthesis.

[$^{14}$C]acetate and [$^{14}$C]pyruvate were used as precursors to measure fatty acid biosynthesis in isolated chloroplasts (B. Liedvogel et al., *Planta*, 169, 481–489 (1986)). [$^{14}$C]acetate incorporation was assayed in a 0.5 ml-volume containing: 50 mM HEPES-NaOH (pH 7.5), 330 mM sorbitol, 5 mM KH$_2$PO$_4$, 10 mM NaHCO$_3$, 1 mM MgCl$_2$,1 mM ATP, 0.1 mM CoA, 0.15 mM [$^{14}$C]acetate (3.33 mCi/mmol), and chloroplasts (20 to 50 μg chlorophyll). [$^{14}$C]pyruvate incorporation into fatty acids was assayed in the same medium except that it included 2 mM TPP, 1 mM NAD$^+$, 0.15 mM [$^{14}$C]-pyruvate (1.33 mCi/mmol), but no acetate. Assay suspensions were illuminated with 1400 μE/m$^2$ sec PAR at 25° C. Assays were initiated by the addition of the labelled substrate and stopped by the addition of 0.5 ml of 40% KOH. To determine the incorporation of radiolabel into a non-polar (fatty acid) fraction, each treatment was saponified at 90° C. for 30 rain in capped vials (P. B. HoJ et al., *Carlsberg Res. Commun.*, 47, 119–141 (1982)). The vials were acidified with 0.5 ml 40% H$_2$SO$_4$, and carrier fatty acids (20 μg each of C 14:0, C 16:0, and C 18:0) were added. The assay mixture was extracted twice with 4 ml hexane. The extracts were combined, dried under N$_2$, and redissolved in 0.3 ml hexane. Aliquots (50 μl) were counted for radioactivity by liquid scintillation spectrometry.

Incorporation of [$^{14}$C]malonyl-Coenzyme A into fatty acids (P. B. Hoj et al., supra; and J. B. Ohlrogge et al., *Proc. Natl. Acad. Sci. USA*, 76, 1194–1198 (1979)) was assayed using cell-free preparations from BMS tissue culture. Cells harvested during logarithmic growth phase were frozen in liquid nitrogen, ground with a mortar and pestle, and thawed in a medium containing: 0.1M HEPES-KOH, pH 7.5; 0.3M glycerol, and 5 mM DTT (buffer:tissue, 2:1, v/w). The homogenate was centrifuged at 12,000 g for 20 min. The supernatant was filtered through miracloth and Centrifuged (125,000 g) for 60 min and then filtered through miracloth and assayed. Assays were conducted at 25° C. in a 0.4 ml volume containing: 1.0 mM ATP, 0.32 mM NADPH, 0.38 mM NADH, 25 μM CoA, 10 μM acetyl-CoA, 25 μg acyl-carrier protein, and 12 μM malonyl-CoA (11.54 μCi/μmol). Reactions were initiated by addition of [$^{14}$C]malonyl CoA and stopped by addition of 0.4 ml 40% KOH. Label incorporation into fatty acids was determined as above. Chlorophyll (D. I. Arnon, *Plant Physiol.*, 24, 1–15 (1949)) and protein (P. K. Smith et al., *Anal Biochem.*, 150, 76–85 (1985)) were determined as described therein.

E. Acetyl-Coenzyme A Carboxylase (ACCase) Activity

Maize chloroplasts, isolated as described above, were suspended in buffer C (0.1M Tricine-KOH, pH 8.0; 03M glycerol, and 1 mM DTT) and homogenized in a glass tissue homogenizer. The disrupted chloroplast fraction was centrifuged at 16,000 g for 15 min. The Supernatant was desalted on a Sephadex G-25 column (1.5×5 cm equilibrated with 0.1M Tricine-KOH, pH 8.0; and 0.3M glycerol) and assayed directly. ACCase activity (B. J. Nikolau et al., *Arch. Biochem. Biophys.*, 211, 605–612 (1981)) was assayed at 30° C. in a 0.2 ml volume which contained 1 mM ATP, 3 mM acetyl coenzyme A, 2.5 mM MgCl$_2$, 50 mM KCl, 0.5 mM DTT, and 15 mM [$^{14}$C]NaHCO$_3$ (0.17 mCi/mmol). Reactions were initiated by addition of acetyl coenzyme A and stopped by addition of 25 μl of 12N HCl. Product formation was determined by the radioactivity found in an acid stable fraction by liquid scintillation spectrometry. Enzyme activity was linear for 15 min.

F. Results

To probe for the site of herbicidal activity of sethoxydim and haloxyfop, labelled acetate, pyruvate, and malonyl-CoA were used individually as precursors for fatty acid synthesis. Isolated chloroplasts from corn seedlings incorporated [$^{14}$C]acetate and [$^{14}$C]pyruvate into a non-polar fraction (fatty acids). Acetate incorporation was linear for 30 min after a 5 min lag period, and dependent upon the addition of free acetyl coenzyme A. Addition of either 10 μM sethoxydim or 1 μM haloxyfop inhibited [$^{14}$C]acetate incorporation into fatty acids by 90% and 89%, respectively, as shown in Table I, below. Sethoxydim (10 μM) and haloxyfop (1 μM) also inhibited the incorporation of [$^{14}$C]pyruvate into fatty acids by 98% and 99%, respectively.

TABLE I

Inhibition of [$^{14}$C]acetate and [$^{14}$C]pyruvate Incorporation into Fatty Acids in Corn Seedling Chloroplasts by Sethoxydim (10 μM) and Haloxyfop (1 μM), 10 minute assay time

|  | Acetate | Pyruvate |
| --- | --- | --- |
|  | Activity (nmol/mg chl min) | |
| Control | 4.4 ± 0.4[1] | 10.8 ± 2.3 |
|  | % Inhibition | |
| Sethoxydim | 90 ± 2.5 | 98 ± 1.1 |
| Haloxyfop | 89 ± 3.1 | 99 ± 0.3 |

[1]Results are expressed as mean of two experiments ± standard error.

The effect of 10 μM sethoxydim and 1 μM haloxyfop on [$^{14}$C]malonyl-CoA incorporation into fatty acids was determined using cell-free extracts from corn suspension cultures. Neither sethoxydim (10 μM) nor haloxyfop (1 μM) inhibited fatty acid synthetase activity. Thus, both herbicides inhibited fatty acid synthesis in intact chloroplasts from corn seedlings with either acetate or pyruvate as a precursor, but did not inhibit incorporation of malonyl-CoA into fatty acids. This suggests that ACCase which catalyzes the formation of malonyl-CoA is the site of action of these herbicides.

EXAMPLE II

Selection and Characterization of Herbicide-tolerant Cell Lines

A selection protocol to identify and isolate herbicide-tolerant maize cells was developed to minimize the adverse effects of high herbicide concentrations on somatic embryo development and plant regeneration capacity. The procedure involved exposing tissue to gradually increasing concentrations of herbicide beginning with a sethoxydim concentration representing 1/20th of lethal dose and doubling the herbicide concentration at approximately two-week intervals until the lethal dose (10 μM sethoxydim) was reached. In this way, the herbicide was allowed to take effect slowly with continuous selection pressure, thus permitting herbicide-tolerant cells to accumulate over time while not affecting the potential for plant regeneration.

A. Selection of a Sethoxydim-Tolerant Cell Line

Many selections were carried out utilizing the selection protocol described in the preceding paragraph. The selection of one such sethoxydim-tolerant cell line that was identified and characterized is described below in detail.

Approximately 100 grams of vigorously growing, regenerable, friable, embryogenic maize callus tissue established from an F$_1$ immature embryo resulting from the cross A188 × B73 were transferred to agar-solidified maintenance medium (Armstrong and Green, *Planta*, 164, 207 (1985)) in petri plates containing 0.5 μM sethoxydim (BASF) (Parsippany, N.J.). This callus line was designated 2167-9/2160-154. Forty plates were prepared and five clumps of callus tissue weighing about 0.5 grams each were placed on each plate. The 0.5 μM sethoxydim concentration was chosen from growth inhibition studies to provide less than 10–20% growth inhibition during the first two weeks of herbicide exposure. After 14 days, 0.25–0.5 g pieces of tissue showing vigorous growth rate and retention of embryogenic morphology (i.e., presence of somatic embryos) were subcultured on fresh medium containing 1.0 μM sethoxydim. Eighty plates containing five pieces of tissue per plate were prepared. For each subsequent transfer, all callus tissue showing growth and somatic embryo forming ability was placed on fresh media containing a two-fold increased sethoxydim concentration. Therefore, callus was transferred at two-week intervals to petri plates containing 0.5, 1.0, 2.0, 5.0 and 10.0 μM sethoxydim. During the course of the selection process, the total number of lines decreased as the herbicide-mediated growth inhibition became more intense. Cell lines exhibiting growth on 10 μM sethoxydim were designated as herbicidetolerant and given an identification number. Two sethoxydim-tolerant lines were recovered that exhibited uninhibited growth at 10 μM sethoxydim. These lines were designated 2167-9/2160-154 S-1 and 2167-9/2160-154 S-2.

B Characterization of Herbicide-Tolerant Maize Cell Line 2167-9/2160-154 S-2

Tolerant cell line 2167-9/2160-154 S-2 ("S-2") was characterized to evaluate: (1) the magnitude of sethoxydim tolerance; (2) cross-tolerance of haloxyfop; and (3) the biochemical basis for the tolerance.

Figure 2:
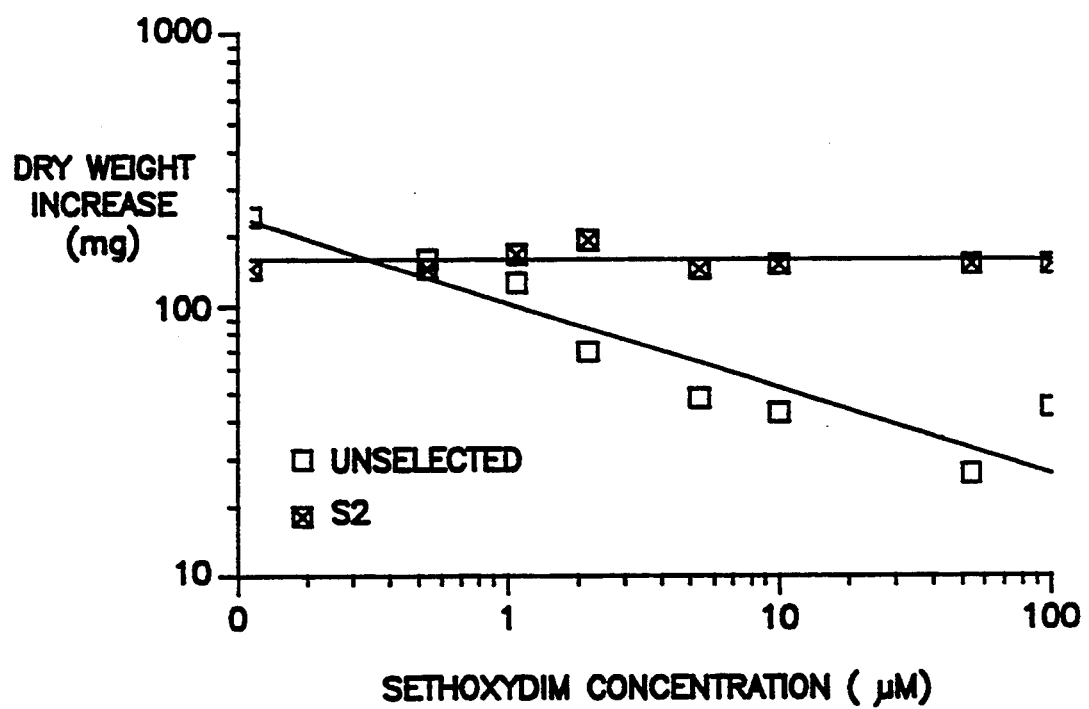
FIG. 2 is a graph depicting the effect of sethoxydim on the growth of mutant maize callus.

Callus tissue from S-2 that had been maintained on 10 μM sethoxydim was transferred to media containing up to 100 μM sethoxydim. One-half gram of S-2 tissue was plated on a 7 cm filter paper as a lawn overlaying 50 ml agar-solidified culture medium containing 0, 0.5, 1.0, 2.0, 5.0, 10.0, 50.0 and 100 μM sethoxydim, and cultured for two weeks. Control cell line 2167-9/2160-154 was plated similarly on medium containing the same levels of sethoxydim. The results of this study are summarized in FIG. 2. The control cell line growth after two weeks was inhibited 50% at 1 μM sethoxydim. Growth of S-2 was not inhibited at 100 μM sethoxydim, indicating that S-2 was at least 100-fold more tolerant than the control callus line.

Growth of S-2 was inhibited with 0.65 μM haloxyfop, whereas the control cell line was inhibited 50% with 0.02 μM, indicating approximately a 30-fold increase in tolerance.

C. Acetyl-Coenzyme A Carboxylase (ACCase) Activity of Maize Cell Line S-2

Assays were conducted to determine if ACCase extracted from cell line S-2 was altered with respect to herbicide activity. ACCase activity of control tissue was 50% inhibited either by 1.5 μM sethoxydim, or by 0.25 μM haloxyfop. ACCase activity of S-2 tissue was inhibited 50% either by 70 μM sethoxydim, or by 1.8 μM haloxyfop, indicating at least 40-fold and 7-fold decreases in herbicide sensitivity on concentration basis, respectively.

EXAMPLE III

Plant Regeneration and Production of Herbicide-Tolerant Seed

A. Plant Regeneration Protocol

Sixteen ca. 150 mg clumps of S-2 callus were transferred per 25×100 mm petri plate containing agar-solidified N6 basal salts and 6% sucrose and incubated 7–14 days in low light (20 μE m$^{-2}$s$^{-1}$). Several plates containing callus on plant regeneration medium were prepared. Callus was transferred to agar-solidified Murashige-Skoog (MS) medium without hormones and incubated in high intensity light (200 μE m-2 s$^-$) for shoot elongation. Developing plants (1–3 cm long) were isolated from the callus surface and transferred to magenta boxes containing agar-solidified MS salts, 2% sucrose with no hormones for two weeks of further growth. When plants reached the 2–3 leaf stage, they were transplanted to peat pots containing potting soil, and were incubated in the growth room until growing stably Surviving plants were transferred to soil in 4" diameter plastic pots and grown in the greenhouse.

Figure 3:
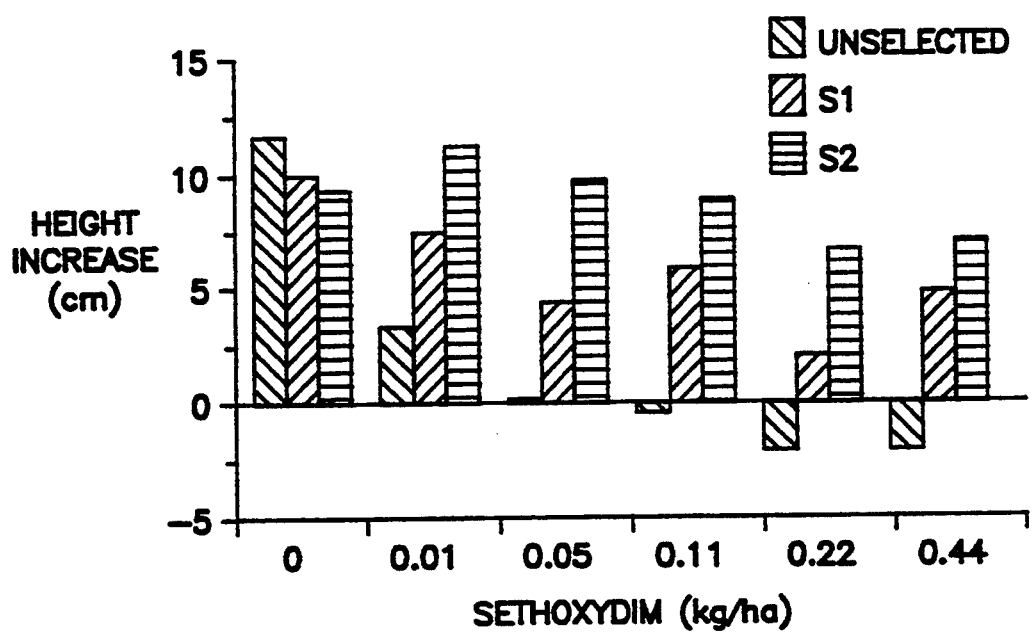
FIG 3 is a graph depicting the shoot length growth of maize seedlings seven days after treatment with sethoxydim.
Figure 4:
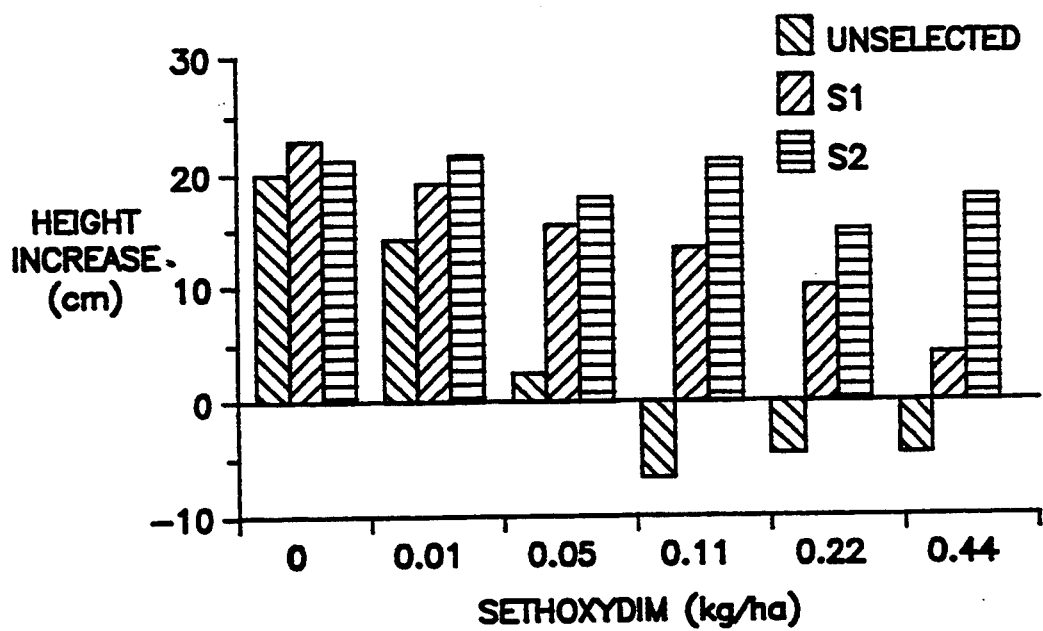
FIG. 4 is a graph depicting the shoot length growth of maize seedlings fourteen days after treatment with sethoxydim.

B. Expression of Herbicide Tolerance in Plants Regenerated from S-2 Callus Tissue Groups of eight control (2167-9/2160-154 unselected) and eight S-2 plants were sprayed with either 0.0, 0.01, 0.05, 0.11, 0.22 or 0.44 kg/ha sethoxydim to determine whole plant sethoxydim-tolerance of greenhouse-grown plants. Control plants were killed by 0.05 kg/ha or more sethoxydim Plants regenerated from the S-2 cell line survived the 0.44 kg/ha sethoxydim treatment, indicating that S-2 plants exhibit at least 20-fold more tolerance of sethoxydim than control. FIG. 3 shows the growth response of the regenerated plants seven days after treatment with 0.44 kg/ha sethoxydim. As shown in FIG. 4, shoot height of regenerated S-2 plants was only slightly reduced 14 days after treatment with 0.44 kg/ha sethoxydim.

C. Seed Production from S-2 Plants

Plants surviving sethoxydim treatments of up to 0.44 kg/ha were transplanted to the genetics plot on the University of Minnesota campus, St- Paul, Minn. Additional S-2 plants were transplanted to the field that had not been sprayed. Sixty-five 2167-9/2160-154 control plants and ninety-five S-2 plants were grown to maturity in the field. Plants were either self-pollinated or cross-pollinated to inbred maize lines A188, A619, A641, A661, A665, B37, B73, R806, and W153R. Control seed were produced by selfing 2167-9/2160-154 regenerated plants, or by crossing them with the inbreds listed above.

D. Expression of Herbicide Tolerance in Progeny of Regenerated Plants

Seeds obtained by the crossing procedure described above were viable and germinated normally. Seeds from thirty S-2 selfed plants and fifteen 2167-9/2160-154 control plants were planted in 25×50 cm trays of soil (28 seeds from each plant in one tray) and grown in the greenhouse. Seedlings at the 3–4 leaf stage were treated with 0.1, 0.44, and 1.1 kg/ha sethoxydim and evaluated for visual herbicide damage and shoot height. Based on visual rating of herbicide damage two weeks after treatment, selfed progeny of S-2 plants segregated approximately 1:2:1 for healthy, uninjured plants: to plants showing partial injury: to dead plants, respectively, at 0.44 and 11 kg/ha sethoxydim treatments. All control progeny of 2167-9 2160-154 control plants were killed by 0.1 kg/ha and greater levels of sethoxydim. These results demonstrate dominant expression of sethoxydim tolerance indicating that sethoxydim tolerance in S-2 plants is a heritable trait. Similar tests were conducted on progeny of S-2 plants crossed to the other inbreds. In all cases, these test cross progeny treated with 0.44 kg/ha sethoxydim segregated 1:1 for growing shoots versus dead shoots whether S-2 plants were used as male or female parents. These results confirm that sethoxydim tolerance is controlled by a single dominant nuclear gene. In all cases, control plants crossed to the other inbreds were killed and therefore sethoxydim-sensitive.

E. Method for Obtaining Uniform Herbicide-Tolerant Seed

Progeny of S-2 plants surviving sethoxydim treatments of 0.44 and 1.1 kg/ha and showing no herbicide injury were transferred to the greenhouse and grown to maturity. These plants may be selfed and their progeny evaluated for sethoxydim and haloxyfop tolerance to identify pure breeding herbicide-tolerant maize lines.

Progeny of S-2 plants crossed to inbred lines and exhibiting sethoxydim tolerance may be recurrently backcrossed to the same inbreds. Progeny of each cross may be screened for sethoxydim-tolerance, and tolerant plants grown to maturity and again crossed to the recurrent parent. After six or seven cycles of backcrossing, sethoxydim-tolerant plants may be selfed and progeny screened for tolerance to produce homozygous sethoxydim tolerant maize inbreds.

EXAMPLE IV

Selection of Additional Herbicide-Tolerant Maize Cell Lines

One primarily sethoxydim-tolerant maize cell line, 2167-9/2160-154 S-1, and two haloxyfop-tolerant maize cell lines, 2167-9/2160-154 H-1 and 2167-9/2160-154 H-2, were selected and characterized as follows:

A Selection of Maize Cell Line 2167-9/2160-154 S-1

Maize cell line 2167-9/2160-154 S-1 was selected from maize cell culture using the protocol described in detail above for the selection of Line 2167-9/2160-154 S-2. Approximately 70 plants were regenerated from Line 2167-9/2160-154 S-1, and either self-pollinated or crosspollinated to the inbred maize lines A188, A619, A641, A661, A665, B37, B73, R806, and W153R.

B. Selection of Maize Cell Line 2167-9/2160-154 H-1

Line 2167-9/2160-154 H-1 was selected from maize cell culture using a similar protocol described in detail above except maize callus tissue was selected using the herbicide haloxyfop. Maize callus tissue was initially plated on 0.01 μM haloxyfop. At two-week intervals, surviving tissue was subcultured onto 0.05, 0.10 and 0.20 μM haloxyfop. Approximately 50 plants were regenerated from Line 2167-9/2160-154 H-1, and were self-pollinated.

C. Selection of Maize Cell Line 2167-9/2160-154 H-2

Line 2167-9/2160-154 H-2 was selected from maize cell culture using a similar protocol described in detail for line 2167-9/2160-154 H-1. No plants have been successfully regenerated from this line.

D. Characterization of Lines 2167-9/2160-154S-1, H-1 and H-2

The tolerant callus cultures were characterized to determine the magnitude of sethoxydim and haloxyfop tolerance. Callus tissue from these lines was evaluated in experiments as described above in the characterization of line 2167-9/2160-154 S-2. Table II summarizes the results of these studies Line 2167-9/2160-154 S-1 and Line 2167-9/2160-154 H-2 showed a four-fold increase in haloxyfop tolerance, while Line 2167-9/2160-154 H-1 exhibited approximately a 60-fold increase in haloxyfop tolerance. Neither haloxyfop selected line showed a significant degree of sethoxydim tolerance, while the sethoxydim selected line S-1 exhibited approximately a 100-fold increase in sethoxydim tolerance.

TABLE II

Herbicide Tolerance of Cell Lines S-1, H-1 and H-2

| Cell Line | Herbicide | |
|---|---|---|
| | Haloxyfop | Sethoxydim |
| 2167-9/2160-154 S-1 | 4[1] | 100 |
| 2167-9/2160-154 H-1 | 61 | 0 |
| 2167-9/2160-154 H-2 | 4 | 0 |

[1] The numbers represent the fold increase in herbicide concentration that results in a 50% reduction in growth of the selected cell lines compared to the unselected control cell line 2167-9/2160-154.

E. Herbicide Inhibition of Acetyl Coenzyme A Carboxylase of Maize Cell Lines S-1, H-1 and H-2

Acetyl Coenzyme A Carboxylase (ACCase) was extracted from cell lines S-1, H-1 and H-2 and assayed as described in detail for maize cell line S-2, above Table III below summarizes the results of these studies. The ACCase from line S-1 was more tolerant of both sethoxydim and haloxyfop, while the ACCase from line H-1 was more tolerant of haloxyfop, but not of sethoxydim. The ACCase from line H-2 showed no difference from the unselected parent line 2167-9/2160-154 in sensitivity to either herbicide.

However, Line H-2 exhibited approximately a five-fold higher level of ACCase activity as compared to the unselected parent: line 2167-9/2160-154. Thus, selection for sethoxydim or haloxyfop tolerance resulted in a less sensitive ACCase in line S-1 and H-1, as well as a higher level of ACCase activity in line H-2.

TABLE III

Herbicide Inhibition of ACCase of Maize Cell Lines S-1, H-1 and H-2

| Cell Line | Herbicide | |
|---|---|---|
| | Haloxyfop | Sethoxydim |
| 2167-9/2160-154 S-1 | 3 | 4 |
| 2167-9/2160-154 H-1 | 7 | 0 |
| 2167-9/2160-154 H-2 | 0 | 0 |

[1] The numbers represent the fold increase in herbicide concentration that inhibits ACCase activity of the selected cell lines by 50% compared to the unselected parent cell line 2167-9/2160-154.

Deposit of Seeds

Seeds from representative S-2 plants (Ex. III (B)) and H-1 plants (Ex IV(B)) have been deposited with the American Type Culture Collection, 12301 Parklawn Drive, Rockville, Md. 20852 USA on Oct. 25, 1988 and assigned accession numbers ATCC 40507, and ATCC 40508, respectively The relevant portions of the publications and patent documents cited herein are hereby incorporated by reference.

The invention has been described with reference to various specific and preferred embodiments and techniques. However, it should be understood that many variations and modifications may be made while remaining within the spirit and scope of the invention.

What is claimed is:

1. A method for combating weeds among maize plants comprising essentially of applying to a planting area for the growing of maize plants an effective quantity of a cyclohexanedione herbicide, an aryloxyphenoxypropanoic acid herbicide, or mixtures thereof, so that weeds are killed and maize plants are uninjured, wherein the growth and development of said maize plants is tolerant to inhibition by a cyclohexanedione herbicide, an aryloxyphenoxypropanoic acid herbicide, or mixtures thereof, and said tolerance is conferred by an acetyl coenzyme A carboxylase (ACCase) tolerant of inhibition by said herbicide at levels which normally inhibit the activity of an ACCase.

2. A method for combating weeds among maize plants according to claim 1 wherein said herbicide is sethoxydim.

3. A method for combating weeds among maize plants according to claim 1 wherein said herbicide is haloxyfop.

4. A method for combating weeds among maize plants according to claim 1 wherein said herbicide is a mixture of sethoxydim and haloxyfop.

5. A method for combating weeds among maize plants according to claim 2 wherein said maize plants are derived from seed S-2 (ATCC 40507).

6. A method for combating weeds maize plants according claim 3 wherein said maize plants are derived from seed H-1 (ATCC 40508).

7. A method for combating weeds among maize plants according to claim 1 wherein said weeds are grass.

8. A method for combating weeds among maize plants consisting essentially of:
   (a) growing in a planting area maize plants wherein the growth and development of said maize plants is tolerant to inhibition by a cyclohexanedione herbicide, and aryloxyphenoxypropanoic acid herbicide, or mixtures thereof, wherein said tolerance is conferred by an acetyl coenzyme A carboxylase (ACCase) tolerant of inhibition by said herbicide at levels which normally inhibit the activity of an ACCase,
   (b) observing the presence of a weed problem among said maize plants of said planting area, and
   (c) applying an effective quantity of a cyclohexanedione herbicide, an aryloxphenoxypropanoic acid herbicide, or mixtures thereof to said maize plants and said weeds present in said planting area so that said weeds are killed and said maize plants are uninjured.

9. A method for combating weeds among maize plants according to claim 8 wherein said herbicide is sethoxydim.

10. A method for combating weeds among maize plants according to claim 8 wherein said herbicide is haloxyfop.

11. A method for combating weeds among maize plants according to claim 8 wherein said herbicide is a mixture of sethoxydim and haloxyfop.

12. A method for combating weeds among maize plants according to claim 9 wherein said maize plants are derived from seed S-2 (ATCC 40507).

13. A method for combating weeds among maize plants according to claim 10 wherein said maize plants are derived from seed H-1 (ATCC 40508).

14. A method for combating weeds among maize plants according to claim 8 wherein said weeds problems is created by the presence of grass in said planting area.

15. A method for combating weeds among maize plants according to claim 9 wherein said herbicide is applied by spraying.

* * * * *

UNITED STATES PATENT AND TRADEMARK OFFICE
CERTIFICATE OF CORRECTION

PATENT NO. : 5,428,001
DATED : June 27, 1995
INVENTOR(S) : David A. Somers et al.

It is certified that error appears in the above-indentified patent and that said Letters Patent is hereby corrected as shown below:

At column 17, line 66, claim 1, please amend "comprising" to --consisting--.

Signed and Sealed this

Nineteenth Day of September, 1995

Attest:

BRUCE LEHMAN

*Attesting Officer*  *Commissioner of Patents and Trademarks*